United States Patent [19]

Green

[11] Patent Number: 4,730,075

[45] Date of Patent: Mar. 8, 1988

[54] CHEMICAL PROCESS INVOLVING ETHERS AND AMINES

[75] Inventor: Michael J. Green, Hedon, England

[73] Assignee: BP Chemicals Limited

[21] Appl. No.: 876,768

[22] Filed: Jun. 20, 1986

Related U.S. Application Data

[62] Division of Ser. No. 647,235, Sep. 4, 1984.

[30] Foreign Application Priority Data

Sep. 7, 1983 [GB] United Kingdom ................. 8323961

[51] Int. Cl.$^4$ .................... C07C 85/18; C07C 102/00; C07C 120/00; C07C 101/00
[52] U.S. Cl. .................................... 558/394; 558/408; 564/152; 564/157; 564/164; 564/168; 564/194; 564/197; 564/343; 564/396; 564/446; 564/471; 560/37; 560/43; 560/125; 560/155
[58] Field of Search ............... 564/343, 396, 446, 471, 564/152, 157, 164, 168, 194, 197; 560/37, 43, 125, 155; 558/394, 408

[56] References Cited

U.S. PATENT DOCUMENTS

4,617,154 10/1986 Green ................................ 558/450

FOREIGN PATENT DOCUMENTS

660480 4/1963 Canada ............................. 564/164
485377 5/1938 United Kingdom ............... 564/471

OTHER PUBLICATIONS

Fieser et al., *Reagents for Organic Synthesis*, vol. 4, pp. 16–18 (1974).

*Primary Examiner*—Glennon H. Hollrah
*Assistant Examiner*—John A. Sopp
*Attorney, Agent, or Firm*—Brooks Haidt Haffner & Delahunty

[57] ABSTRACT

A process for the production of (1) an ether or (2) a second amine comprises reacting an activated olefin with respectively an alcohol or first amine in the presence of a catalyst which is either (a) an amidine or (b) a Lewis base and epoxide. The same catalyst may also be used to carry out the reverse reaction in which an activated olefin and an alcohol or first amine are produced from the appropriate ether or second amine.

7 Claims, No Drawings

CHEMICAL PROCESS INVOLVING ETHERS AND AMINES

This is a division of application Ser. No. 647,235, filed 9/4/84.

The present invention relates to a process for the production of ethers and amines by the reaction of an activated olefin with either an alcohol or an amine.

Journal of the American Chemical Society Volume 65 p 437–439 (1943) describes the reaction of an alcohol with an activated olefin, for example acrylonitrile or methyl acrylate, to produce an ether using as catalyst an alkoxide such as sodium methoxide or a strongly basic ion exchange resin.

It has now been discovered that such reactions can be carried out in the presence as catalyst of either an amidine or a Lewis base and an epoxide. Further, the same catalyst may be used to catalyse the related reaction between a first amine and an activated olefin to produce a second amine.

Accordingly, the present invention provides a process for the production of (1) an ether or (2) a second amine which process comprises reacting an activated olefin with (1) an alcohol or (2) a first amine in the presence of an effective amount of catalyst characterised in that the catalyst is (a) an amidine or (b) a Lewis base and an epoxide.

By activated olefin is meant any olefin which contains at least one electron withdrawing group bonded to an olefinically unsaturated carbon atom. The olefin may be a linear, branched or cyclic olefin or it may be one containing more than one double bond. The electron withdrawing group is a group whose tendency is to withdraw electron density via delocalisation of a negative charge from the carbon-carbon double bond to which it is indirectly attached. Examples of such groups are —COOR, —COR, —CONR$_2$ or —CN where R is an alkyl or aryl group. Suitable activated olefins are those which can undergo the Michael Reaction and include esters of acrylic, methacrylic and crotonic acids, acrylonitrile, acrylamide, alkyl vinyl ketones and their substituted equivalents.

The alcohol reactant may be any alcohol or thioalcohol but is conveniently an aliphatic alcohol or thioalcohol. Preferred alcohols include methanol, ethanol, propanol, butanol, ethylene glycol, propylene glycol, phenol and the like.

The first amine which can be used as a reactant is either a primary or secondary amine, i.e. it is an amine having a hydrogen atom bound directly to the nitrogen atom. Suitable amines which may be used as reactants include the lower monoalkylamines e.g. methylamine, ethylamine and propylamine, lower dialkylamines e.g. dimethylamine, diethylamine and ammonia. The ethers or second amines which are produced by the reaction have the respective genera formulae

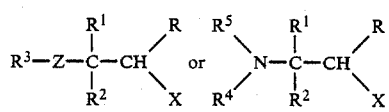

where

R$^1$, R$^2$, and R are hydrogen, X or hydrocarbyl radicals.

R$^3$ is a hydrocarbyl radical preferably a lower aliphatic hydrocarbyl radical.

R$^4$ and R$^5$ are hydrocarbyl radicals, preferably lower aliphatic hydrocarbyl radical or hydrogen Z is either oxygen or sulphur X is an electron withdrawing group.

By the term amidine is meant a compound containing the grouping

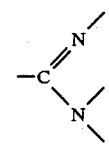

Conveniently the free valencies on the nitrogen atoms are attached to carbon atoms or hydrogen and the free valency on the carbon atom to another carbon atom or nitrogen. In the last case the structure will comprise a guanidine grouping.

A preferred class of amidines is the cyclic amidines. Cyclic amidines are defined as those amidines wherein at least one of the nitroIgen atoms is part of an alicyclic or heterocyclic substituted or unsubstituted hydrocarbyl ring. In the case where the amidine is a guanidine then any two of the three nitrogen atoms may be in the same or different rings. Those nitrogen atoms which are not part of any said ring may form part of a substituted or unsubstituted hyrocarbyl group.

A preferred class of cyclic amidine is that in which the amidine group can form part of a fused ring system containing 6 and 5 membered rings or 6 and 7 membered rings or two six membered rings, as for example in 1,5-diazabicyclo [4.3.0]non-5-ene which has the formula

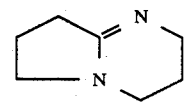

or 1,8-diazabicyclo [5.4.0] undec-7-ene of the formula

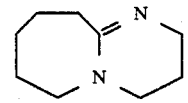

or 1,5,7-triazabicyclo [4.4.0] dec-5-ene of formula

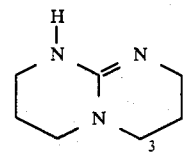

As an alternative to an amidine, the catalyst may also be a Lewis base and an epoxide. The term Lewis base is well known and refers to a compound containing an unshared pair of electrons capable of sharing with an acid. The terms Lewis base and amidine are not therefore mutually exclusive.

The Lewis base can be an organic compound containing trivalent nitrogen or phosphorus for example an amine or phosphine.

Example of epoxides which can be used are alkylene oxides, e.g. ethylene oxide, aromatic epoxides, e.g. styrene oxide, or substituted epoxides, e.g. 2-ethoxypropanol. Suitably, however, the epoxide is a substituted or unsubstituted $C_2$–$C_8$ alkylene oxide. Preferred epoxides are ethylene oxide, propylene oxide and butylene oxide and the like.

Although, as described above, the catalysts used are soluble in the reaction mixture the reaction can also be carried out in the presence of (i) an amidine or (ii) a Lewis base and epoxide catalyst supported on an inert solid which is insoluble in the reaction medium.

In the case of such supported amidine catalysts, the surface atoms of the solid are chemically bonded to one or more of the free valencies of the amidine or guanidine group either directly or through an intermediate hydrocarbyl radical. In the case of cyclic amidines or guanidines the hydrocarbyl radical may constitute part of the ring structure of the molecule.

As an alternative to a supported amidine, a supported Lewis base in combination with an epoxide can be used. In these catalysts it is convenient to support the Lewis base on the inert solid and have the epoxide compbnent present in solution with the reactants. Any Lewis base can be used but it is preferably selected from the group comprising mono-, di- and tri-alkylamines, alkylphosphines, arylamines and arylphosphines. Compounds containing more than one amine or phosphine group can be used. The amine or phosphine is preferably bonded to the inert solid through one or more of the hydrocarbyl groups attached to the nitrogen or phosphorus atom. Prefrrred examples of amines or phosphines which can be supported on the inert solid are derivatives of trimethylamine, trimethylphosphine, tributylamine, tributylphosphine and the like wherein one or more of the hydrocarbyl groups have been modified in such a way that they are bondable to the surface of the solid.

An alternative to having the Lewis base bonded to the inert solid and the epoxide in solution with the reactants is to have the epoxide bonded to the solid and the Lewis base in solution.

The inert solid may be either organic, such as a resin or a polymer, e.g. polystyrene, a polystyrene/divinylbenzene copolymer, a polyacrylate, polypropylene and the like, or inorganic such as a silica, clay, diatomaceous earth, zeolite, alumina or aluminosilicate.

Commercial examples of the supported base catalysts are TBD supported on polystyrene or polystyrene/divinylbenzene copolymer, Amberlite IRA-93, Amberlyst A21 and Duolite A375.

The amidine or Lewis base is present on the solid in amounts corresponding to between 0.1 and 10 moles per gram of solid.

It is clearly important that the solid is not degraded under the conditions of the particular application for which it is used. Hence by the term 'inert solid' is meant a solid which does not undergo physical or chemical degradation under the reaction conditions.

Although the reaction can be carried out at or below ambient temperature, it is in most cases desirable to work at elevated temperature to increase reaction rates. The temperature of the reaction can however be in the range 0° to 200° C., preferably in the range 20° to 100° C.

In addition to the reactants described above, a solvent can also be added to the reaction mixture. The solvent should be inert to both of the reactants under the reaction conditions and is preferably one which is miscible with both the reactants.

It has also been discovered that the catalyst described above will also catalyse the breakdown of the ether or second amine to the activated olefin and an alcohol or first amine.

Accordingly, an embodiment of the invention comprises a process for the production of an activated olefin and an alcohol or a first amine from respectively an ether or second amine as described previously which process comprises contacting the ether or second amine with an effective amount of a catalyst characterised in that the catalyst is (i) an amidine or (ii) a Lewis base and epoxide.

The embodiment may be carried out under conditions similar to those described previously, but in order to drive the reaction it is necessary to remove the alcohol or first amine from the reaction mixture as it is formed in order to prevent equilibrium being reached. The alcohol or first amine is conveniently removed from the reaction mixture by overhead distillation either alone or as an azeotrope with the activated olefin.

Both reactions may be operated either continuously or batchwise.

The invention is illustrated by the following examples.

EXAMPLE 1

A 250 ml round-bottomed flask, fitted with a thermocouple pocket and a water cooled condenser, was charged with 35 g of methanol, 25 g of methyl acrylate, and 0.5 g of 1,5,7-triazabicyclo[4.4.0]dec-5-ene (TBD). The contents of the flask were refluxed for 2 hours. Analysis of the cooled liquid product by gas chromatography showed that all the methyl acrylate had been converted to the methyl ester of 3-methoxy propionic acid.

COMPARATIVE EXAMPLE A

Example 1 was repeated in the absence of TBD. Analysis of the liquid product indicated that no reaction had occurred.

EXAMPLE 2

Example 1 was repeated except that 0.5 g of 1,8-diazabicyclo[5.4.0]undec-7-ene was used as a catalyst in place of TBD. Analysis of the liquid product showed a methyl acrylate conversion of 95% to methyl 3-methoxypropionate.

EXAMPLE 3

Example 1 was repeated except that 0.5 g of 1,5-diazabicyclo[4.3.0]non-5-ene was used as a catalyst in place of TBD. Analysis of the liquid product showed a methyl acrylate conversion of 99% to methyl 3-methoxypropionate.

EXAMPLE 4

Example 1 was repeated except that 0.5 g of tetramethylguanidine was used as a catalyst in place of TBD. Analysis of the liquid product showed a methyl acrylate conversion of 92% to methyl 3-methoxypropionate.

EXAMPLE 5

Example 1 was repeated except that 0.5 g of triethylamine and 1 g of butene oxide were used as a catalyst in place of TBD. Analysis of the liquid product showed a 50% conversion of methyl acrylate to methyl 3-methoxypropionate.

COMPARATIVE EXAMPLE B

Example 5 was repeated in the absence of butene oxide. Analysis of the liquid product indicated that no reaction had occurred.

EXAMPLE 6

Example 5 was repeated except that 0.5 g of pyridine was used in place of triethylamine. Analysis of the liquid product showed a methyl acrylate conversion of 67% to methyl 3-methoxypropionate.

EXAMPLE 7

Example 5 was repeated except that 0.5 g of N-methyl imidazole was used in place of triethylamine. Analysis of the liquid product showed a methyl acrylate conversion of 82% to methyl 3-methoxypropionate.

EXAMPLE 8

A solution containing 35 g of methanol, 0.5 g of polyvinylpyridine, and 1 g of propene oxide was heated to 100° C. in a sealed Fischer-Porter tube under an initial nitrogen pressure of 50 psi. On cooling, the resulting mixture was transferred to the apparatus described in Example 1 (an additional 10 g of methanol was used to transfer residual solid to the flask). 25 g of methyl acrylate was added and the resulting mixture refluxed for 2 hours. Analysis of the liquid product showed a methyl acrylate conversion of 34% to methyl 3-methoxypropionate.

EXAMPLE 9

Example 1 was repeated except that 25 g of methyl methacrylate was used in place of methyl acrylate. Analysis of the liquid product showed a methyl methacrylate conversion of 19% to methyl 3-methoxy-2-methylpropionate.

EXAMPLE 10

Example 1 was repeated except that 25 g of methyl vinyl ketone was used in place of methyl acrylate. Analysis of the liquid product showed that all the methyl vinyl ketone had been converted to 4-methoxybutan-2-one.

EXAMPLE 11

Example 10 was repeated except that 25 g of ethanol was used in place of methanol. Analysis of the liquid product showed that all the methyl vinyl ketone had been converted to 4-ethoxybutan-2-one.

COMPARATIVE EXAMPLE C

Example 11 was repeated in the absence of catalyst. Analysis of the liquid product indicated that no 4-ethoxybutan-2-one had been produced.

EXAMPLE 12

Example 1 was repeated except that 25 g of acrylonitrile was used in place of methylacrylate. Analysis of the liquid product showed that all the acrylonitrile had been converted to 3-methoxypropionitrile.

EXAMPLE 13

A solution containing 2 g of diethylamine, 2 g of ethyl acrylate, and 0.1 g of 1,5,7-triazabicyclo[4.4.0]dec-5-ene was maintained at room temperature for 2 hours 50 min. Analysis of the liquid product by gas chromatography showed an ethyl acrylate conversion of 44% to the ethyl ester of 3-diethylaminopropionic acid.

COMPARATIVE EXAMPLE D

Example 13 was repeated in the absence of catalyst. Analysis of the liquid product showed an ethyl acrylate conversion of only 27% to the ester of 3-diethylaminopropionic acid.

EXAMPLE 14 - Reverse reaction of those described above

A 250 ml round-bottomed flask was charged with 100 g of methoxypropionitrile, 5 g of methanol and 1 g of 1,5,7-triazabicyclo[4.4.0]dec-5-ene. The temperature in the flask was raised to 140° C. and a colourless liquid (55 g) distilled out. Subsequent analysis of the distillate by gas chromatography showed it to contain by weight 48% methanol, 41.5% acrylonitrile and 2% methoxypropionitrile.

The advantage of the catalysts described above over those previously described for these reactions is their complete solubility in both reactants and products.

I claim:

1. A process for the production of a second amine, said second amine having the formula

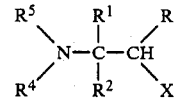

where
- $R^1$, $R^2$, and $R$ are hydrogen, $X$ or hydrocarbyl radicals, $R^4$ and $R^5$ are hydrocarbyl radicals or hydrogen, and
- $X$ is an electron withdrawing group, which process comprises reacting an activated olefin with a first amine,
said activated olefin being one which can undergo the Michael Reaction, and said first amine being selected from the group consisting of methylamine, ethylamine, propylamine, dimethylamine, diethylamine and ammonia, in the presence of an effective amount of a catalyst, characterised in that the catalyst is
(a) an amidine, or
(b) a Lewis base and epoxide.

2. A process as claimed in claim 1 characterised in that the amidine is a cyclic amidine.

3. A process as claimed in claim 1 characterised in that the amidine is a cyclic guanidine.

4. A process as claimed in claim 1 characterised in that the Lewis base is an organic compound containing trivalent nitrogen or trivalent phosphorus.

5. A process as claimed in claim 1 characterised in that the catalyst is supported on an inert support which is insoluble in the reaction mixture.

6. A process as claimed in claim 1 characterised in that the activated olefin comprises an olefin with at least one electron withdrawing group bonded to an olefinically unsaturated carbon atom.

7. A process as claimed in claim 1 characterised in that the Lewis base is a trialkylamine, pyridine, a polymeric amine or a trialkylphosphine.

* * * * *